United States Patent [19]
Hollister

[11] Patent Number: 5,139,489
[45] Date of Patent: Aug. 18, 1992

[54] NEEDLE PROTECTION DEVICE

[75] Inventor: William H. Hollister, Nelson, N.H.

[73] Assignee: Smiths Industries Medical Systems, Inc., Keene, N.H.

[21] Appl. No.: 663,454

[22] Filed: Mar. 4, 1991

Related U.S. Application Data

[63] Continuation-in-part of Ser. No. 637,714, Jan. 7, 1991, abandoned.

[51] Int. Cl.$^5$ .............................................. A61M 5/32
[52] U.S. Cl. ..................................... 604/192; 128/763
[58] Field of Search ................... 128/760, 763, 770; 604/192, 198

[56] References Cited

U.S. PATENT DOCUMENTS

| | | |
|---|---|---|
| 1,779,451 | 10/1930 | Sponsel . |
| 2,700,385 | 1/1955 | Ortiz . |
| 2,836,942 | 6/1958 | Miskel . |
| 2,854,976 | 10/1958 | Heydrich . |
| 2,953,243 | 9/1960 | Roehr . |
| 3,021,942 | 2/1962 | Hamilton . |
| 3,073,307 | 1/1963 | Stevens . |
| 3,074,542 | 1/1963 | Myerson et al. . |
| 3,255,873 | 6/1966 | Speelman . |
| 3,294,231 | 12/1966 | Vanderbeck . |
| 3,323,523 | 6/1967 | Scislowicz et al. . |
| 3,329,146 | 7/1967 | Waldman, Jr. . |
| 3,333,682 | 8/1967 | Burke . |
| 3,367,488 | 2/1968 | Hamilton . |
| 3,485,239 | 12/1969 | Vanderbeck . |
| 3,537,452 | 11/1970 | Wilks . |
| 3,610,240 | 10/1971 | Harautuneian . |
| 3,658,061 | 4/1972 | Hall . |
| 3,828,775 | 8/1974 | Armel . |
| 3,890,971 | 6/1975 | Leeson et al. . |
| 3,904,033 | 9/1975 | Haerr . |
| 3,934,722 | 1/1976 | Goldberg . |
| 3,968,876 | 7/1976 | Brookfield . |
| 4,113,090 | 9/1978 | Carstens ............... 206/365 |
| 4,139,009 | 2/1979 | Alvarez . |
| 4,175,008 | 11/1979 | White ..................... 128/759 |
| 4,300,678 | 11/1981 | Gyure et al. ............ 206/364 |
| 4,375,849 | 3/1983 | Hanifl ..................... 206/366 |
| 4,430,082 | 2/1984 | Schwabacher ........ 604/263 |
| 4,502,744 | 6/1986 | Jagger et al. ........... 604/192 |

(List continued on next page.)

FOREIGN PATENT DOCUMENTS

WO87/07162 12/1987 World Int. Prop. O. .

Primary Examiner—Max Hindenburg
Attorney, Agent, or Firm—Pollock, Vande Sande & Priddy

[57] ABSTRACT

To be used with a double-ended needle assembly and to prevent the accidental pricking of user, or others, in a first embodiment of the present invention, a container holder mated with the needle assembly has a protective housing integrally and flexibly connected thereto. To prevent a contaminated needle from posing a risk to the user and others, the housing connected to the container holder is pivoted into alignment with the contaminated needle such that the needle is retained by at least one locking mechanism integral of the housing. The container holder, along with the contaminated needle assembly, can then be disposed of. If the container holder were to be reused, a second embodiment of the present invention provides for the connection of a protective housing to the hub of a double-ended needle assembly. For this embodiment, after use, the contaminated needle assembly, after having been properly retained in the protective housing, is removed from the reusable container housing and disposed of. Another embodiment of the invention relates to integrally and flexible connecting a protective housing to an adapter, which is interposed between the double-ended needle assembly and the container holder. Variants of the invention include a collapsible housing having a sealer therein which may be used to sealingly secure the tip of the contaminated needle and a collapsible hinge which likewise is used to effect the securing of the tip of the contaminated needle in a sealer adapted to the distal end portion of the housing.

17 Claims, 11 Drawing Sheets

U.S. PATENT DOCUMENTS

| | | | |
|---|---|---|---|
| 4,634,428 | 1/1987 | Cuu | 604/110 |
| 4,643,722 | 2/1987 | Smith, Jr. | 604/192 |
| 4,659,330 | 4/1987 | Nelson et al. | 604/192 |
| 4,664,259 | 5/1987 | Landis | 604/192 |
| 4,664,654 | 5/1987 | Strauss | 604/198 |
| 4,681,567 | 7/1987 | Masters et al. | 604/198 |
| 4,695,274 | 9/1987 | Fox | 604/198 |
| 4,702,738 | 10/1987 | Spencer | 604/198 |
| 4,728,320 | 3/1988 | Chen | 604/110 |
| 4,728,321 | 3/1988 | Chen | 604/110 |
| 4,731,059 | 3/1988 | Wanderer et al. | 604/192 |
| 4,735,311 | 4/1988 | Lowe et al. | 604/263 |
| 4,735,618 | 4/1988 | Hagen | 604/192 |
| 4,737,144 | 4/1988 | Choksi | 604/198 |
| 4,738,663 | 4/1988 | Bogan | 604/198 |
| 4,734,233 | 5/1988 | Schneider | 604/192 |
| 4,747,836 | 5/1988 | Luther | 604/198 |
| 4,747,837 | 5/1988 | Hauck | 604/198 |
| 4,772,272 | 9/1988 | McFarland | 604/198 |
| 4,778,453 | 10/1988 | Lopez | 604/110 |
| 4,781,697 | 11/1988 | Slaughter | 604/192 |
| 4,782,841 | 11/1988 | Lopez | 604/198 |
| 4,790,828 | 12/1988 | Dombrowski et al. | 604/198 |
| 4,795,432 | 1/1989 | Karczmer | 604/110 |
| 4,795,443 | 1/1989 | Permenter et al. | 604/198 |
| 4,801,295 | 1/1989 | Spencer | 604/198 |
| 4,804,372 | 2/1989 | Laico et al. | 604/198 |
| 4,813,426 | 3/1989 | Haber et al. | 128/763 |
| 4,816,022 | 3/1989 | Poncy | 604/198 |
| 4,816,024 | 3/1989 | Sitar et al. | 604/192 |
| 4,819,659 | 4/1989 | Sitar | 604/198 |
| 4,820,277 | 4/1989 | Norelli | 604/192 |
| 4,826,490 | 5/1989 | Byrne et al. | 604/198 |
| 4,826,491 | 5/1989 | Schramm | 604/198 |
| 4,838,871 | 6/1989 | Luther | 604/192 |
| 4,842,587 | 6/1989 | Poncy | 604/198 |
| 4,846,796 | 7/1989 | Carrell et al. | 604/110 |
| 4,850,968 | 7/1989 | Romano | 604/110 |
| 4,850,976 | 7/1989 | Heinrich et al. | 604/192 |
| 4,850,977 | 7/1989 | Bayless | 604/198 |
| 4,850,978 | 7/1989 | Dudar et al. | 604/201 |
| 4,850,994 | 7/1989 | Zerbst et al. | 604/198 |
| 4,850,996 | 7/1989 | Cree | 604/198 |
| 4,858,607 | 8/1989 | Jordan et al. | |
| 4,863,434 | 9/1989 | Bayless | 604/198 |
| 4,863,435 | 9/1989 | Sturman et al. | 604/198 |
| 4,863,436 | 9/1989 | Glick | 604/198 |
| 4,867,746 | 9/1989 | Dufresne | 604/192 |
| 4,872,552 | 10/1989 | Unger | 604/110 |
| 4,874,383 | 10/1989 | McNaughton | 604/198 |
| 4,874,384 | 10/1989 | Nunez | 604/198 |
| 4,883,469 | 11/1989 | Glazier | 604/192 |
| 4,886,503 | 12/1989 | Miller | 604/192 |
| 4,888,001 | 12/1989 | Schoenberg | 604/192 |
| 4,892,107 | 1/1990 | Haber | 128/763 |
| 4,892,521 | 1/1990 | Laico et al. | 604/192 |
| 4,900,309 | 2/1990 | Netherton et al. | 604/192 |
| 4,950,249 | 8/1990 | Jagger et al. | 604/192 |
| 4,966,591 | 10/1990 | Yuen | 604/192 |
| 4,976,699 | 12/1990 | Gold | 604/192 |

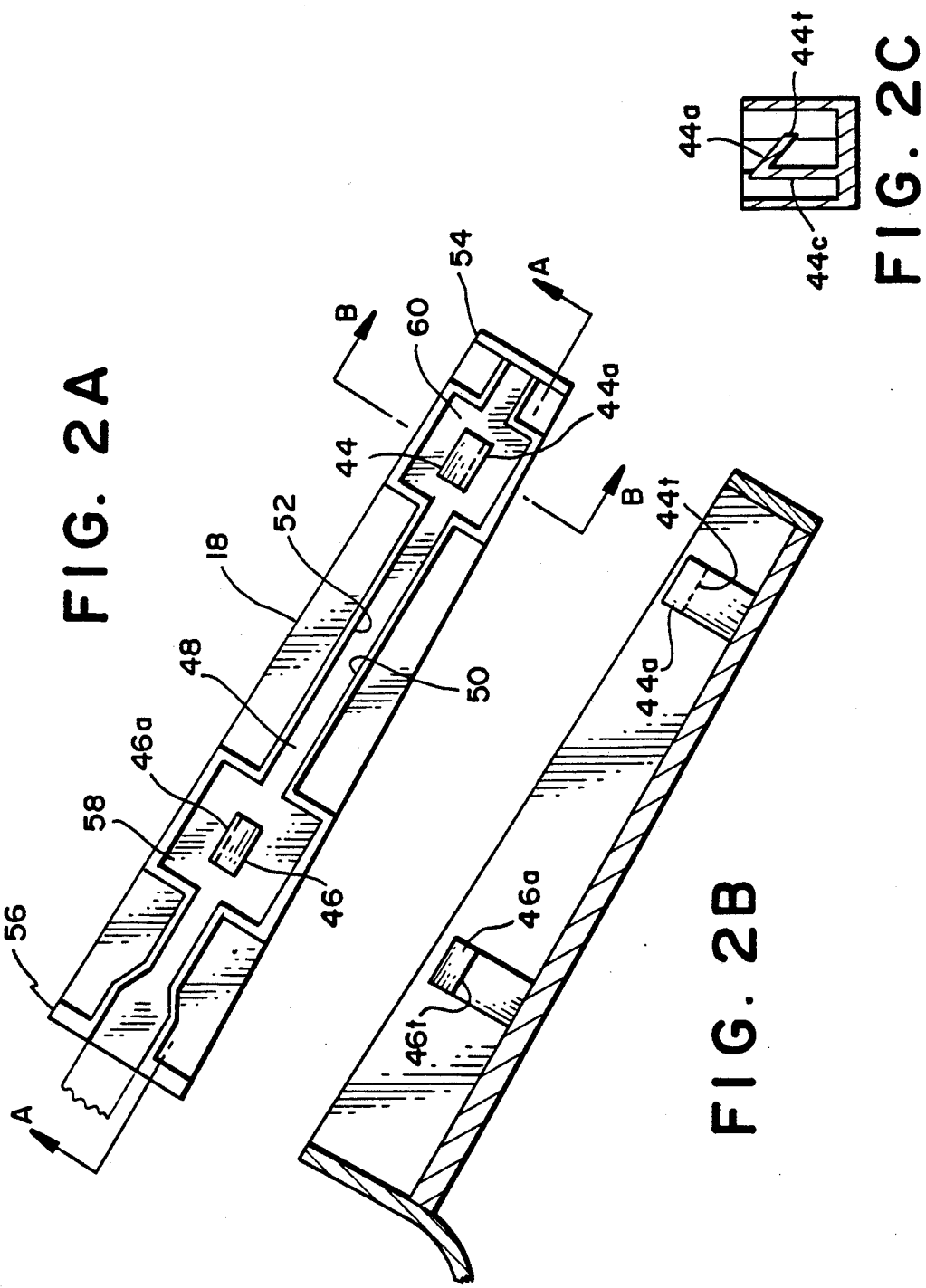

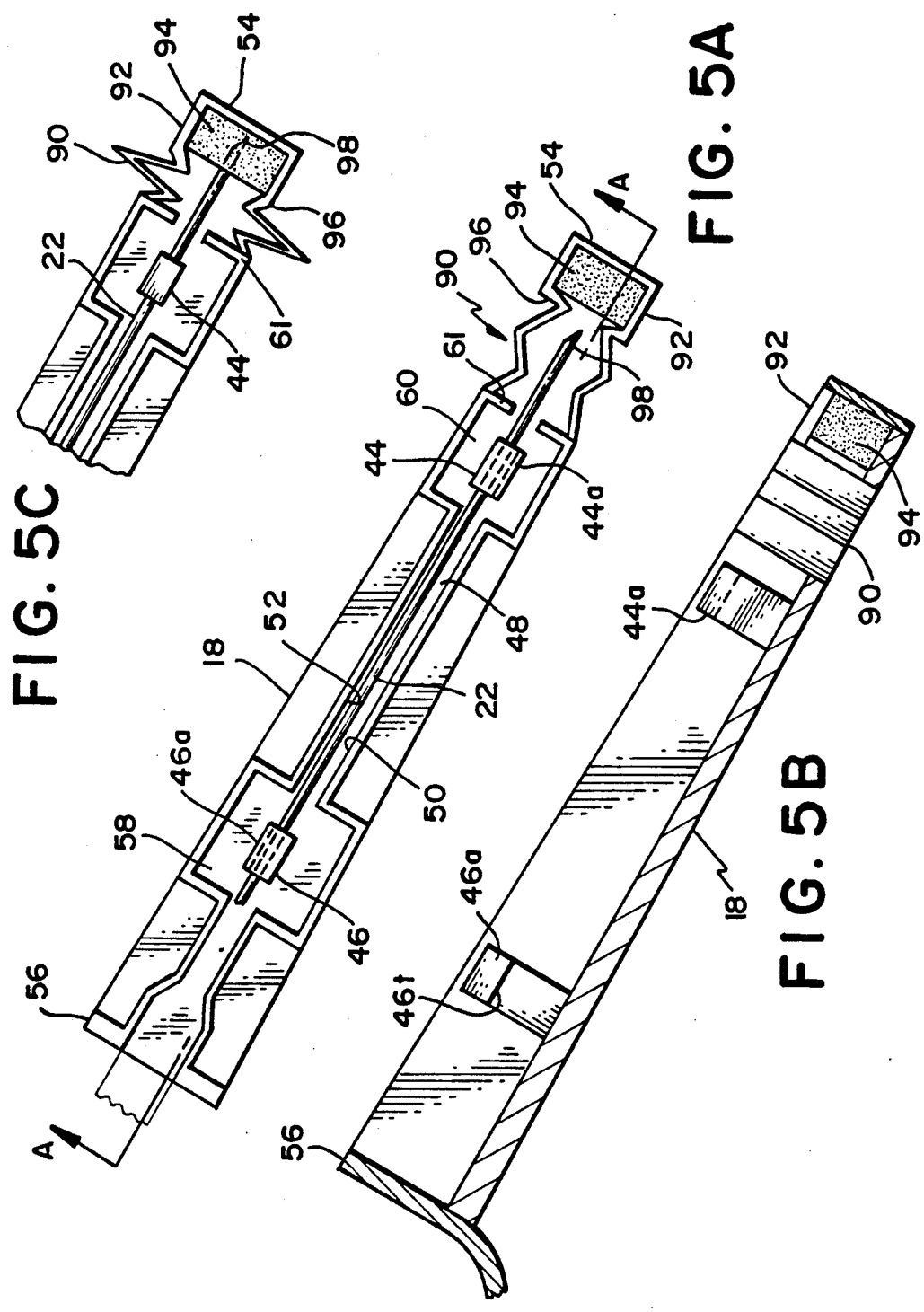

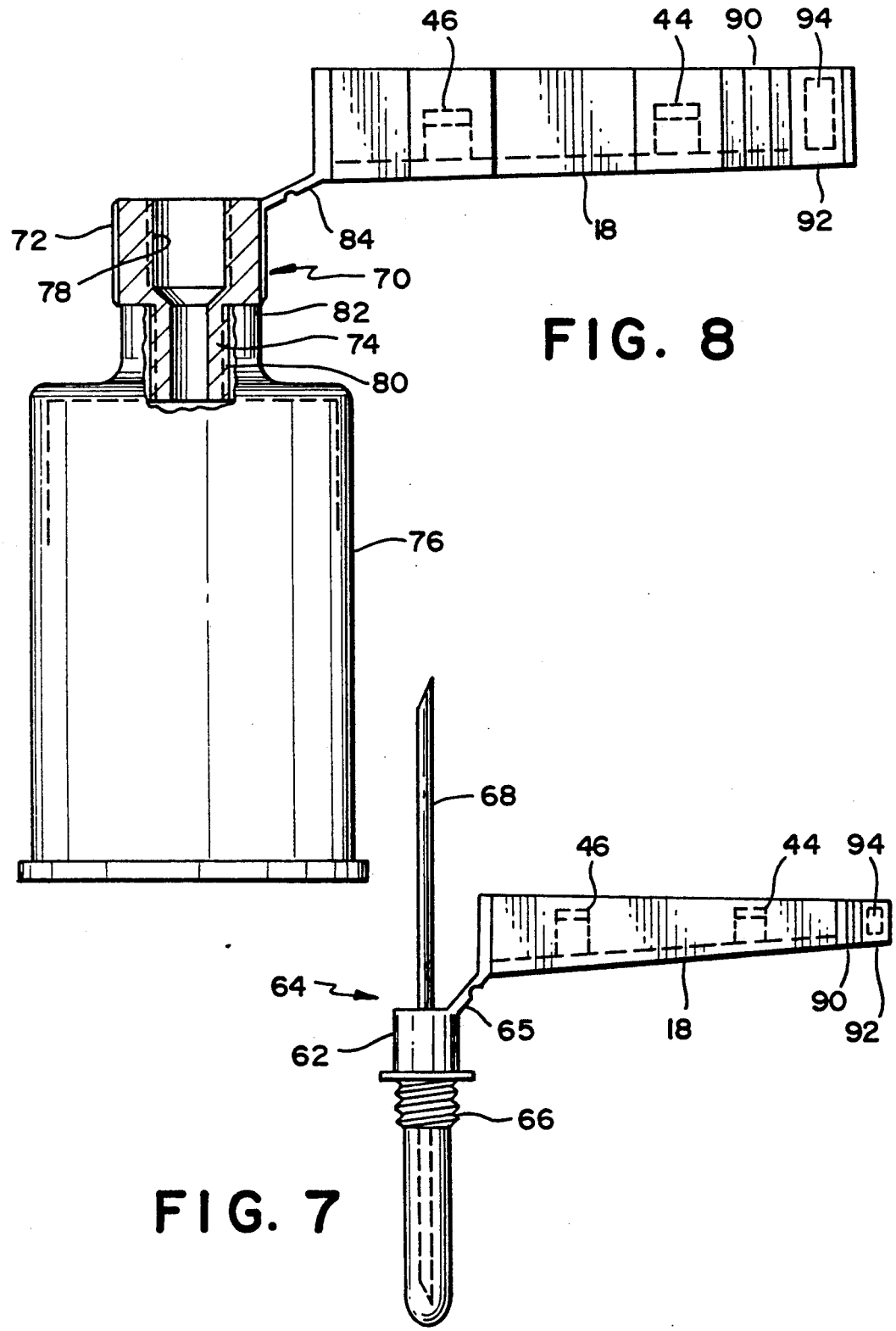

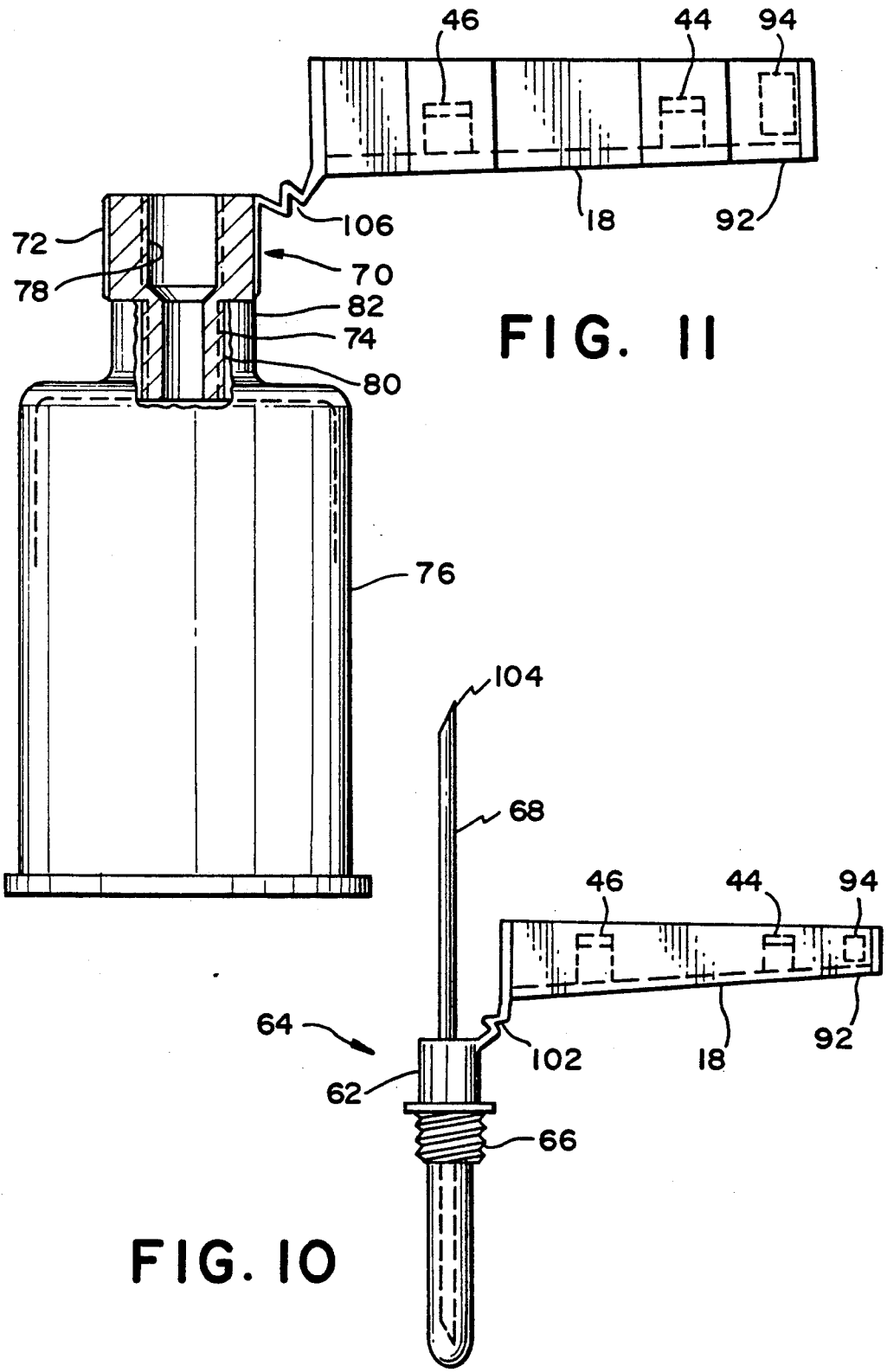

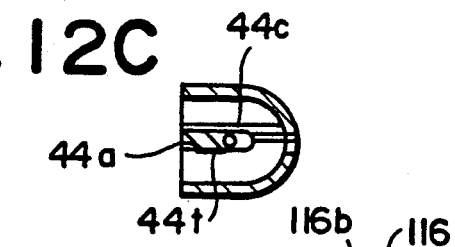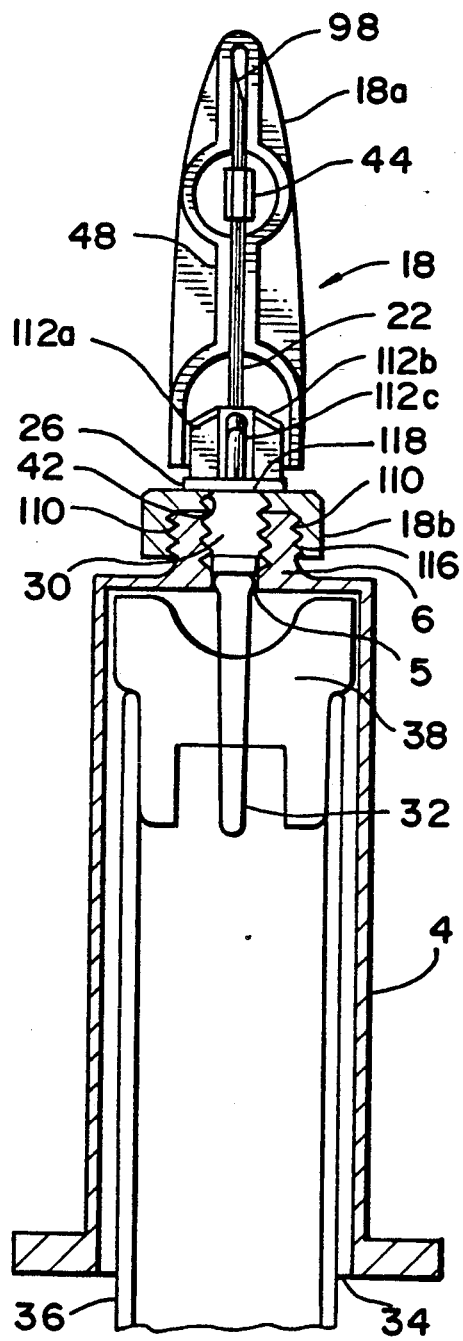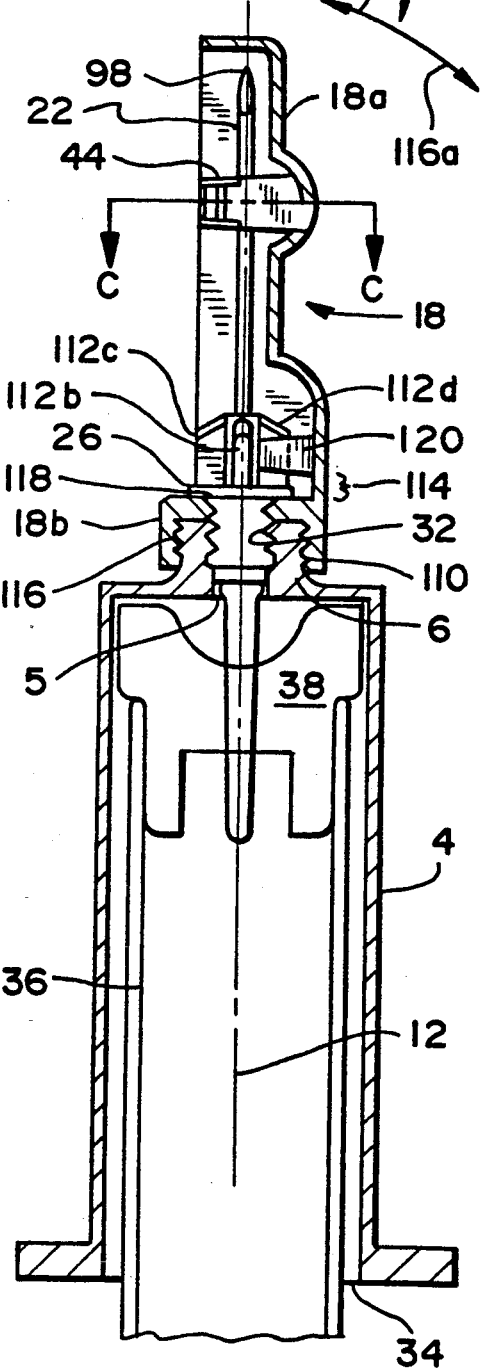

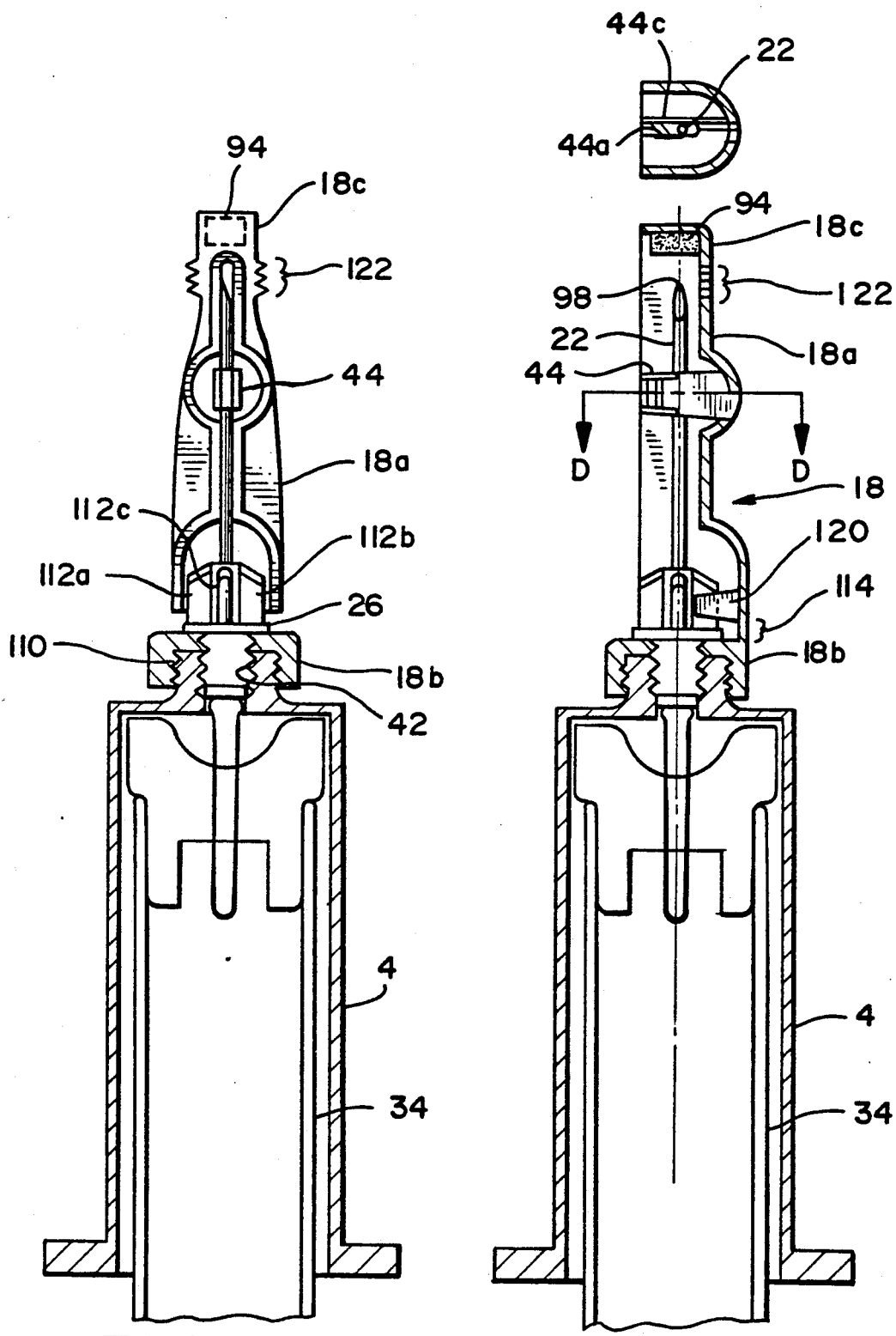

FIG. 14A
FIG. 14B
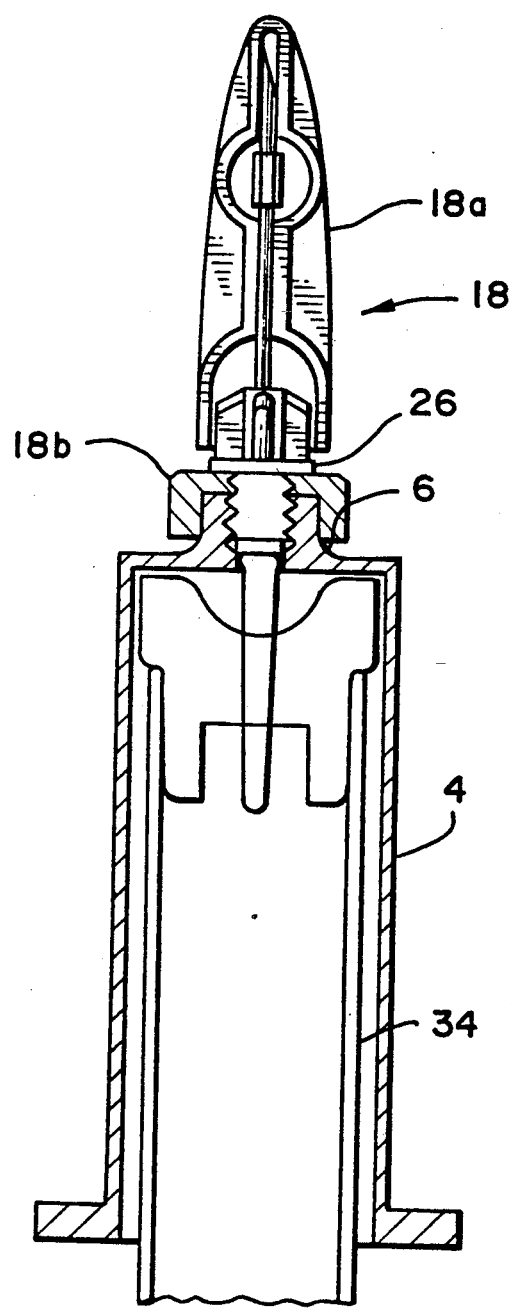
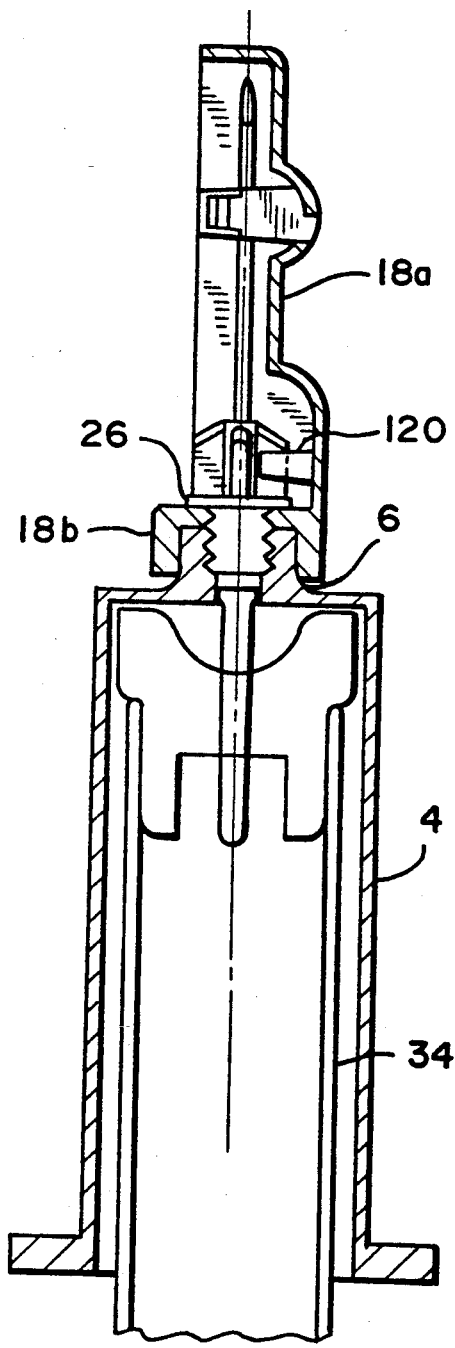

NEEDLE PROTECTION DEVICE

This is a Continuation-In-Part application of patent application Ser. No. 637,714, abandoned filed Jan. 7, 1991.

FIELD OF THE INVENTION

This invention relates to co-pending application Ser. No. 532,558, entitled "Safety Needle Container", filed Jun. 4, 1990, now U.S. Pat. No. 4,982,842, by the same inventor and assigned to the same assignee as the instant invention. The disclosure of the '842 Patent is hereby incorporated to this application by reference. This invention is further related to co-pending application Ser. No. 561,459, entitled "Safety Needle Container", filed Aug. 1, 1990 by the same inventor and assigned to the same assignee as the instant invention. The disclosure of the '459 application is also hereby incorporated to this application by reference.

Specifically, the present invention is related to a protective device which can be used with a fluid holding tube and, more specifically, a protective device to prevent a user, or a bystander, from being accidently pricked by the sharp end of a needle assembly that is used in conjunction with the fluid collection tube.

BACKGROUND OF THE INVENTION

In the '558 and '459 applications, different protective devices to be used with a hypodermic needle are disclosed. As enunciated therein, protective devices for preventing a user, or for that matter a bystander, from being accidently pricked by the sharp end of an exposed needle are urgently needed, particularly in view of the current epidemic of infectious diseases resulting from sharing of, and possibly accidentally pricking by, contaminated needles.

In the case where a double-ended needle assembly is used with a fluid collection system, for example an evacuated blood collection tube, the risk of a user, i.e. a phlebotomist, of accidentally puncturing himself with a contaminated needle is magnified, inasmuch as, ordinarily, the user has to recap the used double-ended needle assembly before removing it from the container holder, which holds the evacuated blood collection tube. Thus, the user has to, in a two-handed operation, first carefully align a protective sheath with the exposed contaminated needle before he is able to cover the latter with the former. As should readily be apparent, if the user is in a hurry, or is distracted as for example in emergency room situations, there is a good chance that he may miss aligning the sheath with the exposed needle and be accidentally pricked thereby, and therefore exposed to the risk of contracting blood-borne infectious diseases.

The double-ended needle assembly oftentimes is removed from the container holder, which is reusable. According to workers skilled in this area of the medical field, some of the reasons given for reusing a container holder include: (1) the extra cost of using a new container holder for each patient; (2) the desire not to clutter up the environment with extra trash; and (3) it is easier for a phlebotomist to carry and use one container holder for all patients, instead of having to carry many container holders and using a new one for each patient.

SUMMARY OF THE PRESENT INVENTION

To eliminate as much as possible the possibility of a user, or a bystander, from being accidentally pricked by a contaminated needle, the inventor proposes, in a first embodiment, that a protective housing (or sheath) with integral locking mechanisms be connected to the fluid container holder such that the housing may be pivoted to envelop the contaminated needle and permanently retain the needle within the housing with the locking mechanisms.

A second embodiment of the present invention connects a protective housing to the hub of a double-ended needle assembly such that the needle assembly—including the housing after the same has been pivoted to permanently retain the contaminated needle—may be thrown out after use, if the container holder is to be reused.

A third embodiment of the present invention integrates a protective housing to an adapter to be interposed between a container holder and a needle assembly such that, once the housing has been pivoted to envelop and retain the contaminated needle, the adapter and the attached needle assembly are both removed and discarded, were the container holder to be reused.

A fourth embodiment of the present invention integrates a protective housing to a base, which is to mate with the outer circumferential portion of the receptacle end of a reusable container holder. There are two variants to this embodiment. The first variant envisions the fittingly mating of the base of the protective housing directly to the receptacle end of the holder. The second variant envisions the receptacle end being externally threaded and the base correspondingly internally threaded, so that the base can threadedly mate with the receptacle end. In either of the variants, the double-ended needle assembly is threadedly mated through an aperture in the base to the inner circumferential threads of the receptacle end. After use both the needle assembly and the protective housing are removed from the container holder at the same time and disposed of.

With the above-noted different embodiments, it is further envisioned that a collapsible (also can be compressible or crushable) section be integrated somewhere along the housing and a sealing material adapted to the distal end of the housing so that the tip of the exposed needle of the needle assembly would penetrate into and be sealingly secured within the sealing material, to thereby ensure that not only is the tip of the contaminated needle not exposed, but that it is also completely sealed.

An alternative to integrating a collapsible section somewhere along the length of the housing is to connect the housing to the holder with a collapsible (compressible or crushable) hinge. Thus, by moving the housing relative to the fluid container holder in the first embodiment, the double-ended needle assembly in the second embodiment, or the adapter in the third embodiment, the tip of the contaminated needle is sealingly secured by the sealing material adapted to the distal end of the housing.

It is, therefore, an objective of the present invention to provide a one piece combination container holder and protective housing/sheath that requires only one-handed operation, and provides for excellent protection to a user or bystander.

It is another objective of the present invention to provide a needle assembly that has its own integral protective housing to thereby eliminate the need for an adapter.

It is yet another objective of the present invention to provide a safety adapter that, along with a contaminated needle assembly, may be safely removed from a container holder, thereby allowing the container holder to be reused.

It is still another objective of the present invention to provide a needle protection device that can substantially sealingly secure the tip of a contaminated needle to thus further enhance the safety integrity of the device.

BRIEF DESCRIPTION OF THE DRAWINGS

The above-mentioned objectives and advantages of the present invention will become more apparent and the invention itself will be best understood by reference to the following description of embodiments of the present invention taken in conjunction with the accompanying drawings, wherein:

FIG. 2A is a plan view of the protective housing shown in the FIG. 1 embodiment;

FIG. 2B is a cross-sectional cut-away view, along line A—A, of the FIG. 2A protective housing;

FIG. 2C is a cross-sectional cut-away view, along line B—B, of the FIG. 2A protective housing;

FIG. 5A is a plan view of another embodiment of the protective housing of the present invention in which a collapsible section is integrally interposed between an end cap portion and a main portion of the housing, and a sealing means having been adaptedly fitted to the cap portion of the housing;

FIG. 5B is a side view of the FIG. 5A protective housing;

FIG. 5C is a plan view of the FIG. 5A housing whose collapsible section has collapsed due to the relative movement of the end portion and main portion of the housing toward each other;

FIG. 7 is a variation of the FIG. 3 embodiment with a FIG. 5A protective housing;

FIG. 8 is a variation of the FIG. 4 embodiment which has a FIG. 5A protective housing;

FIG. 10 is another variation of the FIG. 3 embodiment whose hinge is collapsible;

FIG. 11 is a variation of the FIG. 4 embodiment, with a collapsible hinge connecting the housing to the adapter;

FIG. 12A is a semi-exposed frontal view of yet another embodiment of the present invention;

FIG. 12B is a semi-exposed side view of the FIG. 12A embodiment;

FIG. 12C is a cross-sectional view along cut C—C of FIG. 12B;

FIG. 13A is a semi-exposed frontal view of a variant of the FIG. 12 embodiment;

FIG. 13B is a semi-exposed side view of the FIG. 13 variant;

FIG. 13C is a cross-sectional view of cut D—D as shown in FIG. 13B;

FIG. 14A is a semi-exposed frontal view of a variant of the FIG. 12 embodiment where the base portion of the housing is fittingly mated to the receptacle end of the container housing; and FIG. 14B is a semi-exposed side view of the FIG. 14A variant embodiment.

DETAILED DESCRIPTION OF THE INVENTION

Figure 1:
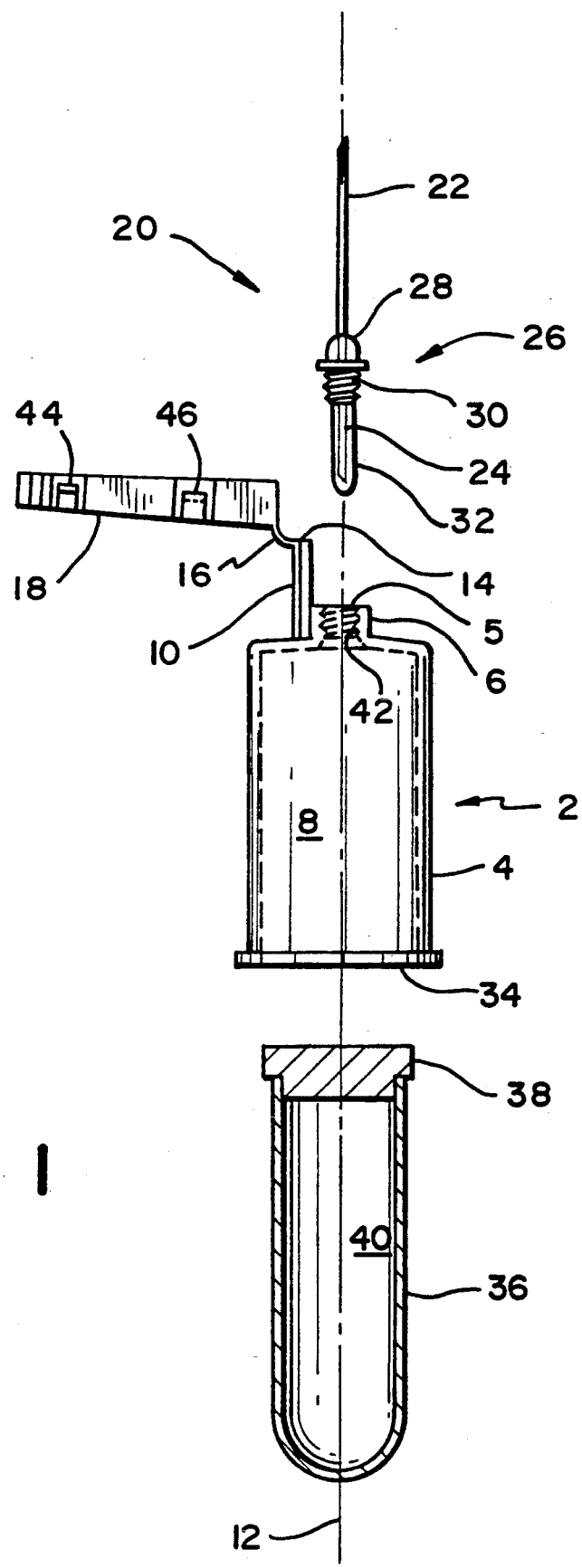
FIG. 1 is a side view of a first embodiment of the safety device of the present invention in alignment with a fluid collection tube and a double-ended needle assembly.

A first embodiment of the present invention, with reference to FIG. 1, shows a fluid container holder 2 having a hollow main body section 4 and a receptacle end 6 integrally extending therefrom. An aperture extends from opening 5 of receptacle end 6 into cavity 8 of main body section 4. The inner circumference of receptacle 6 is threaded.

Integrally connected to main body section 4, and a portion of receptacle end 6, is a substantially rigid shoulder member 10 extending longitudinally in parallel relationship to longitudinal axis 12. At the distal end 14 of shoulder member 10 there is connected, via a hinge means such as living hinge 16, a protective housing or sheath 18. It should be appreciated that instead of utilizing shoulder member 10, hinge 16 can directly connect housing 18 to either receptacle end 6 or main body section 4, or both, since each of the respective lengths of both hinge 16 and housing 18 may be varied to suit different circumstances, i.e. differences in the length of the needles to be enveloped. A more detailed discussion of housing 18 is to be given with reference to FIGS. 2A-2C. A variant of housing 18 is further to be discussed with reference to FIGS. 5A to 5C.

Also shown in alignment along longitudinal axis 12 is a double-ended needle assembly 20 that includes a first needle portion (cannula) 22 and an opposed needle portion (cannula) 24. A needle hub 26 which comprises a protruding portion 28 and a threaded portion 30 is molded about the double-ended needle portions 22 and 24, as shown in FIG. 1. Connected to the lowermost end of threaded portion 30 and covering cannula 24 is a rubber sheath 32.

Container holder 2 further has an open end 34 through which a fluid container tube 36 may be passed into cavity 8 of main body section 4. Container 36 has intimately fitted thereto, at its open end, a rubber stopper 38. Ordinarily most of the air in the container tube has been evacuated such that a vacuum exists within chamber 40 of tube 36. Putting it differently, the pressure inside chamber 40 of tube 36 has a lower pressure than the ambient atmospheric pressure.

For venipuncture operation whereby blood is drawn from a patient, needle assembly 20 is threadedly mated with receptacle 6, via threaded portion 30 and internal threads 42, respectively. Once thus mated, as should readily be apparent, at least a portion of cannula 26 of needle assembly 20 would extend into cavity 8 of main body section 4 of holder 2. At this point the phlebotomist would insert (or invasively contact) the exposed cannula 22 into the vein of the patient. Consequently, blood passes, mostly due to venous pressure, through cannulas 22 and 24 of needle assembly 20. Sheath 32 prevents blood from escaping from the needle assembly into cavity 8 of holder 2.

Once cannula 22 has properly penetrated the patient, to collect, in this instance, blood from the patient, the phlebotomist would insert fluid container tube 36, through open end 34, into cavity 8 of holder 2 such that rubber stopper 38 pushes rubber sheath 32 forward away from cannula 24. At the same time, rubber stopper 38 is pierced by cannula 24. As cannula 24 pierces through rubber stopper 38, since chamber 40 is in essence a vacuum chamber, the blood to be collected from the patient is drawn into chamber 40. As is well known, a number of container tubes may be used to collect multiple tubes of blood from the patient.

As is further well known, the apparatus shown in FIG. 1 may also be used to collect fluids, other than blood, from a living body. For example, urine and amniotic fluids may be withdrawn from a patient by using the same double-ended type needle assembly, albeit with different lengths. Further, instead of an evacuated container tube such as 36 shown in FIG. 1, a fluid container tube in the form of a vial containing medicament may be inserted into cavity 8 of holder 2 such that, with the help of a plunger, the medicament may be forced into the patient. Thus, holder 2 shown in FIG. 1 is adapted to be used to enable fluid passage (both ways) between the patient and a fluid container tube.

When an appropriate amount of fluid has been either withdrawn from or fed to the patient, cannula 22 is withdrawn from the patient. At this time, to ensure that the user, or a bystander, would not be accidently punctured by contaminated cannula 22, housing 18 is pivoted about distal end 14, via hinge 16, such that it comes into alignment with needle assembly 22, i.e. along longitudinal axis 12. As housing 18 comes into alignment with cannula 22, the locking mechanisms, in the form of hooks 44 and 46 integral within housing 18, would first bias against and then snap over cannula 22 to thereby fixedly retaining the contaminated cannula within housing 18. Accordingly, accidental pricking by an exposed contaminated cannula is prevented.

With reference to the plan view of housing 18 shown in FIG. 2A, it can be seen that longitudinal housing 18 has an elongated slot 48, bounded by sides 50 and 52, running substantially in parallel along the length of the housing, which has a tip 54 at the cap (or apex) portion of the housing and a base 56 supporting the main portion of the housing. (For a one-handed operation, a user would push the cap portion against a stationary object to pivot housing 18 into alignment with cannula 22.) Further shown on housing 18 are openings 58 and 60, at whose respective centers are integrally formed locking mechanisms 46 and 44. Locking mechanisms 44 and 46 each have a substantially rigid finger 44a, 46a.

As more clearly shown by the cross-sectional FIG. 2C view of locking mechanism 44, as housing 18 is pushed into alignment with cannula 22, cannula 22 is first biased against finger 44a. But as cannula 22 is pushed past tip 44t of finger 44a, the previously biased finger 44a would spring back into its natural position to thereby retain cannula 22 within the space between finger 44a and extension 44c and substantially prevent relative movement between cannula 22 and housing 18.

FIG. 2B is a cross-sectional view, along cut A—A of FIG. 2A, of housing 18 which shows that fingers 46a and 44a extend in opposite downwardly sloped directions. Such a construction makes it more difficult for a retained contaminated cannula from being forcibly removed from the housing.

A second embodiment of the present invention is envisioned for those instances where it may be desirable to reuse the same container holder. Specifically, with reference to FIG. 3, it can be seen that a housing 18 has now been integrally and flexibly connected to a base, or hub, 62 of a double-ended needle assembly 64 via a living hinge 65. Needle assembly 64 comprises a threaded portion 66, which is to threadedly mate with a receptacle end of a container holder, such as holder 2 (sans housing 18 connected thereto) shown in FIG. 1. The same operation as that discussed previously with reference to FIG. 1 is repeated herein with the notable exception that instead of disposing container holder 2 as was the case in the first embodiment, for the FIG. 3 embodiment, once housing 18 has been pivoted into alignment with cannula 68 so that the same is substantially fixedly retained within housing 18, needle assembly 64—and of course housing 18 integral thereof, may be removed from the receptacle end of the container holder and disposed of. The FIG. 3 embodiment is more cost effective than the FIG. 1 embodiment insofar as the container holder is now reusable.

Figure 4:
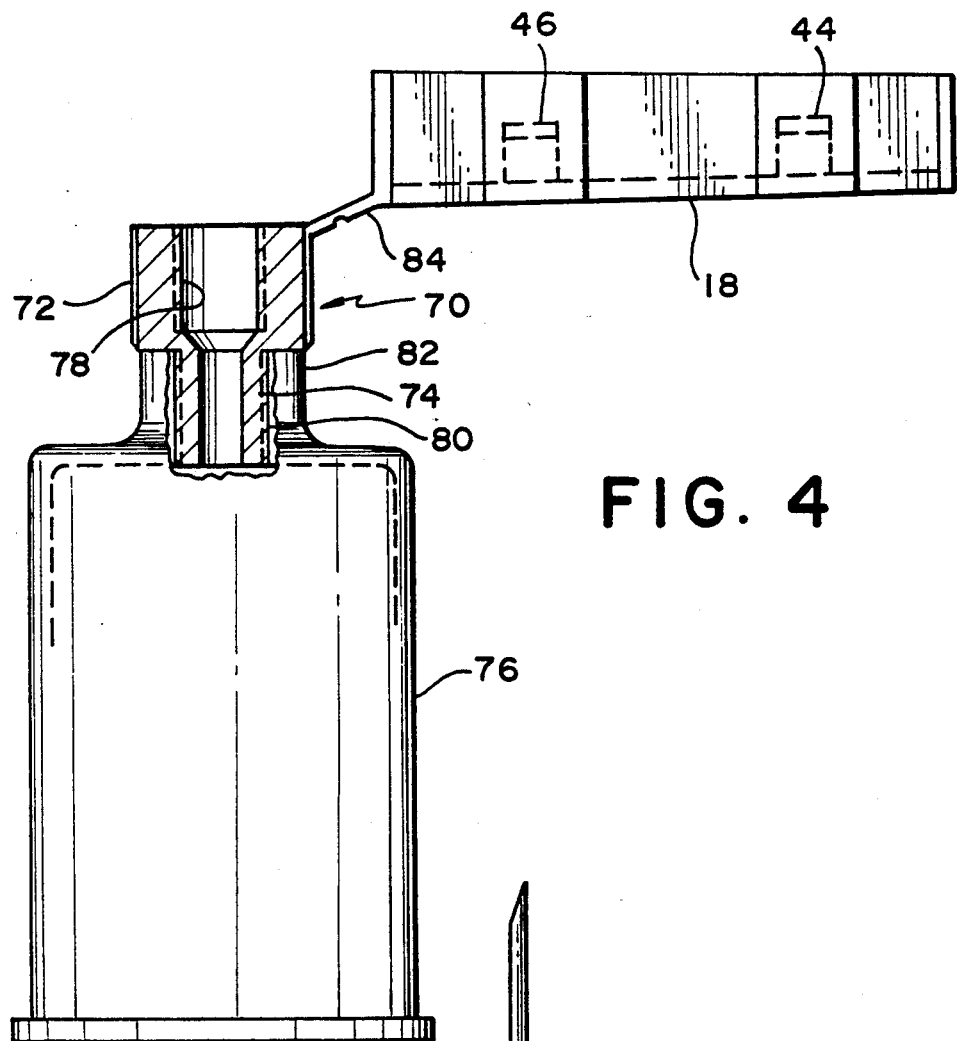
FIG. 4 is another embodiment of the present invention utilizing an adapter, with an integrally connected protective housing, to be interposed between a needle assembly and a fluid container holder.

Yet another embodiment of the present invention is illustrated in FIG. 4. There it can be seen that an adapter 70 comprises a section 72 and a smaller section 74 integrally extending therefrom. Adapter 70 is to be interposed between a fluid container holder 76 and a needle assembly such as 20 shown in FIG. 1. To accommodate needle assembly 20, the inner circumference of section 72 is threaded so that threaded portion 30 of needle assembly 20 (see FIG. 1) may be threadedly mated with the internal threads (indicated by dash lines 78) of section 72. To mate with container holder 76, external threads (indicated by dash lines 80) are used to threadedly mate with corresponding internal threads of receptacle end 82 of container holder 76. Once needle assembly 20 has been threadedly mated with section 72 and receptacle end 82 threadedly mated with section 74, the operation of the FIG. 4 embodiment proceeds as was discussed previously.

For the FIG. 4 embodiment, however, housing 18 is integrally and flexibly connected to section 72 of adapter 70 via a living hinge 84. After the contaminated cannula has been withdrawn from the patient, to prevent accidental pricking, housing 18 is, like the previous embodiments, pivoted into alignment with the contaminated cannula and snapped into a retention relationship, with locking mechanisms 44 and 46, within housing 18. To dispose of the contaminated needle assembly, adapter 70 is removed from container holder 76. For this embodiment, container holder 76 is likewise reusable.

With reference to FIGS. 5A—5C, a variant of the FIG. 2A housing may also be used with the instant invention to further ensure that the tip of the exposed needle (or cannula) is sealingly secured, and therefore not exposed, even in highly unlikely circumstances where the protective housing may not properly retain the contaminated needle—as for example when the housing is cracked or the locking mechanisms malfunctioned. For this variant, the same elements, or those performing the same functions, as the embodiments shown in FIGS. 1-4 are labelled the same.

As illustrated in FIG. 5A, variant housing 18 has a substantially longitudinal collapsible (compressible or crushable) accordion-shaped section 90 interposed between and integrally connecting the main portion and a cap portion 92 of housing 18. For purposes of explanation, the main portion of housing 18 extends from base 56 to a partition 61 at the end of opening 60. If the housing is a single piece molded sheath, manufactured for example from plastic, collapsible section 90 may be an integral part of housing 18 which integrally extends from partition 61 to edge 96 of cap, or apex, portion 92. Alternatively, collapsible section 90 may be made of materials different from that of the m in portion of housing 18, or cap portion 92, as for example foldable cardboard or fibered paper.

Although collapsible section 90 is shown as accordion-shaped, it should be appreciated that other shaped collapsible sections may also be used so long as section 90 may collapse (or be compressed) to reduce the distance separating cap portion 92 (or more accurately edge 96 of cap portion 92) and partition 61, as relative movement urging the main portion of housing 18 and cap portion 92 toward each other is effected.

Adapted to and fitted within cap portion 92 is a sealing material 94 which may be, for example, a malleable elastomer, a piece of rubber or some other suitable material which can sealingly secure and firmly grip a sharp object that penetrates therein, as for example tip 98 of needle 22 Materials such as cork or wax may also be used. It should further be appreciated that tip 54 of cap portion 92 is made of a material such as hard plastic that is substantially impervious to penetration by sharp objects such as, for example, tip 98 of needle 22. As was discussed previously, the length of housing 18, which extends from base 56 to tip 54, may vary depending on the length of needle 22, and is such that clearance is provided in the space within collapsible section 90 to allow a needle of a given length to pass unobstructed through opening 52, when housing 18 is pivoted to substantially align along the longitudinal axis of needle 22 and to envelop the same.

Assume that housing 18 has been pivoted into alignment with the longitudinal axis of needle 22 and that needle 22 has in turn been retained by locking mechanism 44. As best shown in FIG. 5C, when relative movement for urging cap portion 92 toward the main portion of housing 18 is effected, as for example illustrated by the reduction of distance between partition 61 and edge 96, collapsible section 90 collapses to thereby allow tip 98 of needle 22 to penetrate into sealing material 94 and be substantially sealingly secured thereby. The relative movement between the main portion of housing 18 and cap portion 92 may be effected by a single-handed operation of pushing tip 54 of housing 18 against some immobile object. FIG. 5B is a side view of the FIG. 5A housing.

Figure 3:
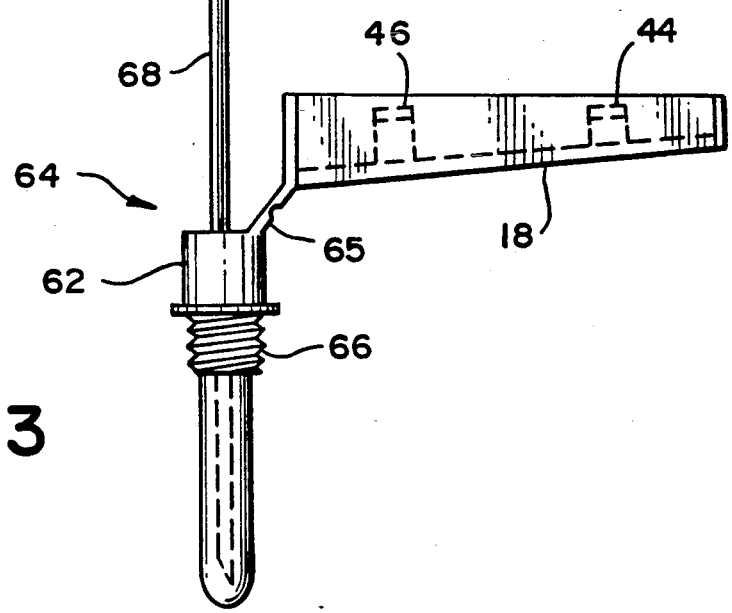
FIG. 3 is a second embodiment of the present invention showing a needle assembly having integrally connected thereto a protective housing.
Figure 6:
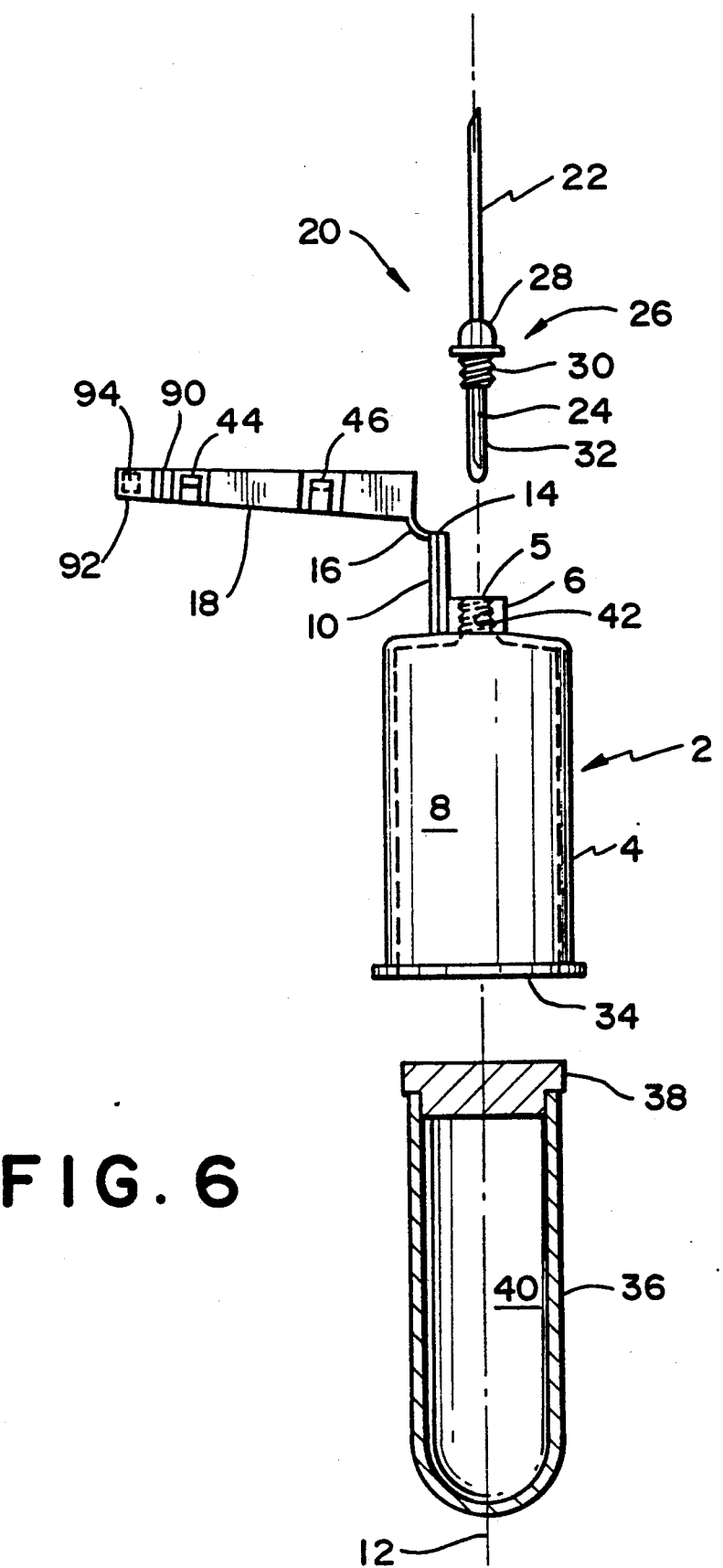
FIG. 6 is a side view of a variation of the FIG. 1 embodiment having the FIG. 5A protective housing.

As shown in FIGS. 6, 7 and 8, the respective housings of the embodiments of FIGS. 1, 3 and 4 have been replaced by the FIG. 5A variant housing. Each of the alternative embodiments of FIGS. 6, 7 and 8 would, of course, provide the additional safety feature of sealingly securing the tip of a contaminated needle, after variant housing 18 has been pivoted into alignment with the contaminated needle and cap portion 92 is urged against the tip of the needle such that the tip of the needle is sealingly secured by sealing material 94 fitted within cap portion 92.

Figure 9:
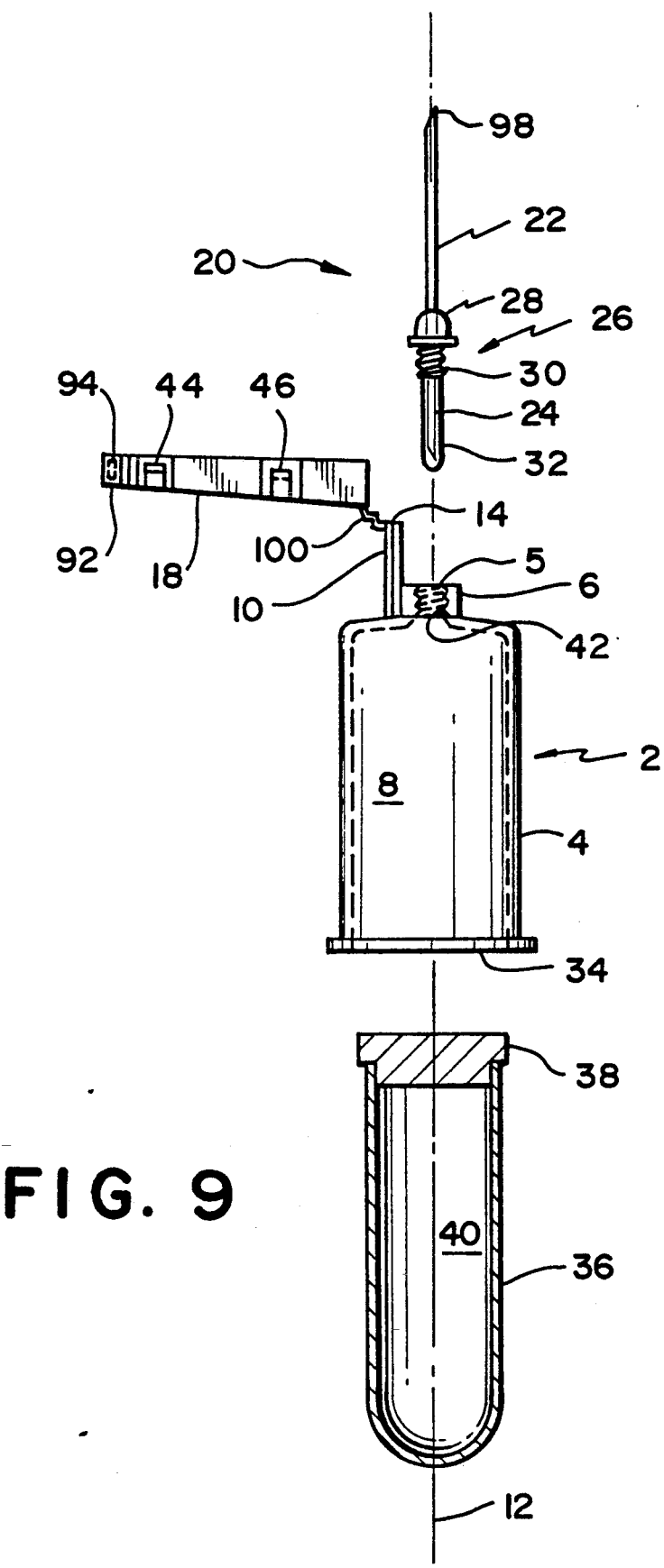
FIG. 9 is yet an another variation of the FIG. 1 embodiment having incorporated thereto a collapsible hinge.

In place of a housing having a main portion jointed to a cap portion by a collapsible section, an alternative embodiment of providing for the secure retention of the tip of a contaminated needle may be had with reference to FIGS. 9, 10 and 11. Again, components in FIGS. 9, 10 and 11 which are similar to, or perform similar functions as, those discussed earlier are labelled the same.

With specific reference to FIG. 9, which is a modification of the FIG. 1 embodiment, it can be seen that housing 18, which is a unitary piece, is flexibly connected to distal end 14 of shoulder member 10 by a collapsible hinge means such as collapsible living hinge 100. Although unitarily constructed, housing 18 nonetheless has a cap portion 92 within which a sealing material 94 is fitted.

As can easily be understood, after housing 18 has been pivoted into alignment position along the longitudinal axis of needle 22, a relative movement may be effected to urge housing 18 and container holder 2 toward each other s that collapsible hinge 100 would collapse, thereby allowing tip 98 of needle 22 to pierce and penetrate into sealing material 94 and be sealingly secured thereby. As should be appreciated, it is not necessary that shoulder member 10 be present, as collapsible hinge 100 may be directly connected to container holder 2, at receptacle end 6 or otherwise.

As shown in FIG. 10, housing 18 of a needle assembly 64 is flexibly connected to needle hub 62 by a collapsible living hinge 102. Adapted to cap portion 92 of housing 18 is a sealing material 94 which sealingly secures tip 104 of cannula 68, after housing 18 has been pivoted to align along the longitudinal axis of cannula 68 and housing 18 and hub 62 are urged relatively toward each other to collapse collapsible hinge 102, and to thereby cause tip 104 to penetrate into sealing material 94.

With reference to FIG. 11, the adapter embodiment of the present invention is shown to have its housing 18 connected to member 70 by a collapsible living hinge 106. As was the case with the FIGS. 9 and 10 embodiments, adapted and fitted to a cap portion 92 of housing 18 is a sealing material 94 which likewise is used to sealingly secure the tip of a contaminated needle assembly, which is threadedly mated to member 70, as was discussed previously with reference to the discussion of the FIGS. 10 and 11 embodiments.

Yet another embodiment of the present invention is shown with reference to FIGS. 12A and 12B where components which are the same or perform similar functions as those discussed earlier are labeled the same. As shown, container holder 4 for this embodiment has a receptacle end 6 whose outer circumferential portion has external threads 110 and whose inner circumference is threaded with internal threads 42. As shown in FIG. 12A, needle assembly 20 containing cannulas 22 and an opposed cannula 24 (not shown in FIG. 12A since it is covered by rubber sheath 32) is threadedly mated to internal threads 42 of receptacle end 6 via its threaded portion 30. The needle assembly is shown has having a needle hub 26 enveloping a portion of cannula 22. For the FIG. 12A embodiment, it should further be noted that needle hub 26 has a number of rib members 112a to 112d each extending orthogonally away from cannula 22.

As best shown in both FIGS. 12A and 12B, this embodiment of the present invention has a housing 18 that has a housing portion 18a extending from a base portion 18b. The portion of the housing designated 114 (best shown in FIG. 12B) is made of a material more flexible than housing 18, or a living hinge such as 16 shown in FIG. 1, so that housing portion 18a can pivot along the directions as indicated by bi-directional arrows 116.

As shown, base portion 18b of housing 18 has internal threads 116 for threadedly mating with threads 110 of receptacle end 6 of container holder 4. Bas portion 18b further has an aperture 118 which comes into alignment with opening 5 of receptacle end 6 when base portion 18b is threadedly mated to receptacle end 6.

As should be appreciated, housing 18 has to be first threadedly mated to container holder 4, via threads 116 of base 18b and threads 110 of receptacle end 6, before the needle assembly is threaded through aperture 118 into opening 5 of receptacle end 6. As should further be appreciated, once base 18b of housing 18 has been securely mated to receptacle end 6 of container holder 4, housing portion 18a has to be biased away from longitudinal axis 12 along the direction indicated by directional arrow 116a in order to permit threaded portion 30 of the needle assembly to be threaded into opening 5 of receptacle 6. Assuming that housing portion 18a remains biased away from cannula 22, once the needle assembly has been assembled as shown in FIGS. 12A and 12B, the insertion of container tube 36 into opening 34 of container holder and the subsequent transferring of fluid between the patient and the container tube 36 via cannula 22 proceeds a described previously with the earlier embodiments. Once the transfer of fluid has been completed, to prevent the user or bystander from being accidentally exposed to contaminated tip 98 of cannula 22, housing portion 18a is pivoted along the direction indicated by directional arrow 116b into substantial alignment along longitudinal axis 12 of the needle assembly. As was discussed before, mechanism 44 of housing portion 18a will retain cannula 22 within the housing portion, i.e. in the space between finger 44a and extension 44c as shown in FIG. 12c.

After cannula 22 has been retained in place, both housing 18 and the needle assembly are removed together from container holder 4 such that container holder 4 may be reused. One example method of ensuring that both housing 18 and the needle assembly are removed as a unit is to have at least one flange member 120 (seen in FIG. 12b) extending internally from housing portion 18a toward rib member 112d, so that, as base 18b is unthreaded from receptacle end 6, flange member 120 would come into contact alignment with one of the rib members of the needle hub 26, for example rib member 112d. And as base portion 18b is further unthreaded from receptacle end 6, the needle assembly is forced by the contact engagement of rib member 112b and flange member 120 to turn in the same direction as base portion 18b. Accordingly, the needle assembly is unthreaded from the container holder together with housing 18. The thus removed combination housing 18 and needle assembly is of course disposed of in the usual manner.

FIGS. 13A to 13C illustrate a variant of the FIG. 12 embodiment whereby a cap portion 18c is jointed to housing portion 18a by a collapsible section 122, which is similar to section 90 of the housing shown in FIG. 5A. The operation of the FIG. 13 embodiment is the same as the FIG. 12 embodiment but for the fact that once cannula 22 has been securely retained within housing portion 18a by locking mechanism 44, relative movement between housing portion 18a and cap portion 18c is effected toward each other to collapse collapsible section 122 to thereby force tip 98 to pierce into sealing member 94 adapted to cap portion 18c. Tip 98 is accordingly securely retained within sealing member 94.

Yet another variant of the FIG. 12 embodiment is illustrated in FIGS. 14A and 14B where it can be seen that external threads 110 of receptacle end 6 and internal threads 116 of base portion 18b (as shown in FIGS. 13A and 13B) have been eliminated. Instead, the outer circumference of receptacle end 6 matches very closely to the inner circumference of base portion 18b of housing 18, such that base 18b may be fittingly mated with the outer circumferential portion of receptacle end 6. With the threading of threaded portion 30 of the needle assembly into aperture 118 of base portion 18b and opening 5 of receptacle end 6, base portion 18b is substantially guaranteed to stay in place, until the combination housing 18 and needle assembly is unthreaded from container holder 4.

With reference to the housing shown in FIGS. 5A–5C and specifically to the embodiments illustrated in FIGS. 6–14, it should be appreciated that the protective device of the instant invention is able to doubly prevent the accidental pricking of a user, or a bystander, by a contaminated needle, inasmuch as the protective device is able to, first, substantially permanently retain the contaminated needle by a protective housing, and, secondly, provide for the sealingly retention of the tip of the contaminated needle.

Inasmuch as the present invention is subject to many variations, modifications and changes in detail, it is intended that all matter described throughout this specification and shown in the accompanying drawings be interpreted as illustrative only and not in a limiting sense. Accordingly, it is intended that the invention be limited only by the spirit and scope of the hereto appended claims.

I claim:

1. A safety device to be used with a needle assembly having a first end for invasively contacting a body and a second end for communicating with a container, comprising:

a holder having a hollow main body section and a receptacle end extending therefrom, said holder further having an open end through which at least a portion of said container is inserted into said main body section, said receptacle end of said holder being mated with said second end of said needle assembly such that at least a portion of said second end extends into said main body section to be in communication with said inserted portion of said container to provide a conduit to said container for fluid passage between said body and said container;

housing means flexibly connected to said holder, and pivotable toward a position in substantial alignment along the longitudinal axis of said needle assembly for enveloping said first end of said needle assembly, said housing means including locking means for substantially fixedly retaining said first end of said needle assembly within said housing means once said housing means has been pivoted to said position.

2. Safety device of claim 1, wherein said housing means comprises a longitudinal sheath having an elongated slot through which said first end of said needle assembly passes when said sheath is pivoted to said position.

3. Safety device of claim 1, wherein said locking means comprises at least one hooking means integral of said housing means for substantially retaining said first end of said needle assembly within said housing means.

4. Safety device of claim 1, wherein said housing means is integrally connected to said receptacle end of said holder by a hinge means.

5. Safety device of claim 1, wherein said housing means is further connected to said main body section of said holder.

6. Safety device of claim 1, further comprising a substantially rigid shoulder member extending from said holder to flexibly connect said housing means.

7. Safety device of claim 1, wherein said container comprises a fluid collection tube having an internal pressure lower than the ambient atmospheric pressure such that, when said conduit is provided between said tube and said body, fluid from said body is drawn and collected in said tube.

8. Safety device of claim 1, wherein said needle assembly comprises a hub; and
wherein said receptacle end of said holder is internally threaded for threadedly mating with said hub of said needle assembly.

9. Safety device of claim 1, wherein said housing means includes at least a cap portion and a main portion from which said housing means is connected to said holder, further comprising:
a collapsible section integrally interposed between said cap and main portions; and
means adapted to said cap portion of said housing means to substantially sealingly secure the tip of said first end of said needle assembly after said housing means has been pivoted to said substantial alignment position and said cap portion and said main portion have been relatively urged toward each other to thereby collapse said collapsible section.

10. Safety device of claim 1, wherein said housing means includes a cap portion, further comprising:
sealing means adapted to said cap portion of said housing means; and
wherein said housing means is integrally connected to said holder by a collapsible hinge means such that, after said housing means has been pivoted via said hinge means to substantially align along the longitudinal axis of said needle assembly to envelop said first end of said needle assembly, and said housing means and said holder have been relatively urged toward each other to collapse said hinge means, the tip of said first end of said needle assembly would penetrate into said sealing means and be substantially sealingly secured thereby.

11. A safety device for a double-ended needle assembly having opposed cannula portions, comprising:
a holder having a hollow main body section and a receptacle end extending therefrom, said holder further having an open end through which at least a portion of a container is insertable into said main body section, said receptacle end of said holder being mated with said needle assembly such that at least a portion of one of said opposed cannula portions of said needle assembly extends into said main body section to be in communication with said insertable portion of said container;
housing means flexibly connected to said holder, and pivotable toward a position in substantial alignment along the longitudinal axis of said needle assembly for enveloping the other of said opposed cannula portions, said housing means including locking means for substantially fixedly retaining said other of said opposed cannula portions within said housing means once said housing means has been pivoted to said position.

12. Safety device of claim 11, wherein said housing means comprises a longitudinal sheath having an elongated slot through which said other of said opposed cannula portions passes when said sheath is pivoted to said position.

13. Safety device of claim 11, wherein said locking means comprises at least one hooking means integral of said housing means for substantially preventing relative motion between said other of said opposed cannula portions and said housing means.

14. Safety device of claim 11, wherein said housing means is further integrally connected to said receptacle end of said holder by a hinge means.

15. Safety device of claim 11, further comprising a substantially rigid shoulder member extending from said holder to flexibly connect said housing means.

16. Safety device of claim 11, wherein said housing means includes at least a cap portion and a main portion from which said housing means is connected to said holder, further comprising:
a collapsible section integrally interposed between said cap and main portions; and
means adapted to said cap portion of said housing means to substantially sealingly secure the tip of said other of said opposed cannula portions after said housing means has been pivoted to said substantial alignment position and said cap portion and said main portion have been relatively urged toward each other to thereby collapse said collapsible section.

17. Safety device of claim 11, wherein said housing means includes a cap portion, further comprising:
sealing means adapted to said cap portion of said housing means; and
wherein said housing means is integrally connected to said holder by a collapsible hinge means such that, after said housing means has been pivoted via said hinge means to substantially align along the longitudinal axis of said needle assembly to envelop said other of said opposed cannula portions, and said housing means and said holder have been relatively urged toward each other to collapse said hinge means, the tip of said first end of said needle assembly would penetrate into said sealing means and be substantially sealingly secured thereby.

* * * * *